United States Patent [19]

Lesser

[11] Patent Number: 5,321,800
[45] Date of Patent: Jun. 14, 1994

[54] GRAPHICAL LANGUAGE METHODOLOGY FOR INFORMATION DISPLAY

[76] Inventor: Michael F. Lesser, 930 S. Harbor City Blvd., Ste. 200, Melbourne, Fla. 32901

[21] Appl. No.: 989,462

[22] Filed: Dec. 10, 1992

Related U.S. Application Data

[63] Continuation of Ser. No. 440,877, Nov. 24, 1989, abandoned.

[51] Int. Cl.5 .......................... G06F 3/14; G06F 15/42
[52] U.S. Cl. .................................... 395/140; 395/161; 395/159; 364/413.02; 364/413.03; 364/188
[58] Field of Search ....................... 395/159, 161, 140; 364/413.02, 413.03, 413.04, 188, 146; 128/709, 710, 712

[56] References Cited

U.S. PATENT DOCUMENTS

| | | | |
|---|---|---|---|
| 3,993,861 | 11/1976 | Baer | 358/142 |
| 4,045,815 | 8/1977 | Griffith et al. | 128/712 X |
| 4,051,522 | 9/1977 | Healy et al. | 128/903 X |
| 4,154,230 | 5/1979 | Lee | 128/700 X |
| 4,344,145 | 8/1982 | Chasek | 395/140 X |
| 4,436,684 | 3/1984 | White | 364/413.01 X |
| 4,489,387 | 12/1984 | Lamb et al. | 364/413.02 X |
| 4,513,753 | 4/1985 | Tabata et al. | 128/706 |
| 4,527,240 | 7/1985 | Kvitash | 364/413.02 |
| 4,570,225 | 2/1986 | Lundy | 364/413.05 |
| 4,598,368 | 7/1986 | Umemura | 364/413.22 X |
| 4,608,635 | 8/1986 | Osterholm | 364/413.22 |
| 4,631,676 | 12/1986 | Pugh | 364/413.01 |
| 4,639,223 | 1/1987 | Keller, Jr. | 364/413.01 X |
| 4,648,028 | 3/1987 | DeKlotz et al. | 364/188 |
| 4,664,125 | 5/1987 | Pinto | 128/710 X |
| 4,675,147 | 6/1987 | Schaefer et al. | 364/188 X |
| 4,729,381 | 3/1988 | Harada et al. | 364/413.03 X |
| 4,794,532 | 12/1988 | Leckband et al. | 364/413.06 |
| 4,805,631 | 2/1989 | Roi du Maroc, II | 128/710 |
| 4,809,705 | 3/1989 | Ascher | 128/710 |
| 4,847,785 | 7/1989 | Stephens | 395/140 |
| 4,996,654 | 2/1991 | Rosenow | 395/140 |
| 5,043,920 | 8/1991 | Malm et al. | 395/140 X |
| 5,140,519 | 8/1992 | Friesdorf et al. | 364/413.03 |

*Primary Examiner*—Raymond J. Bayerl
*Attorney, Agent, or Firm*—Antonelli, Terry, Stout & Kraus

[57] ABSTRACT

An icon-based method of generating a display indicating the status of each of a number of physical parameters in a monitored physical system and interventions introduced to adjust the physical system. Each parameter and intervention is assigned an area on a display screen, and in each area an image is displayed representing the condition of the associated parameter. Each image includes at least one icon representing an associated condition of the physical parameter. A parameter of the icon is controlled to indicate the status of the associated condition.

13 Claims, 4 Drawing Sheets

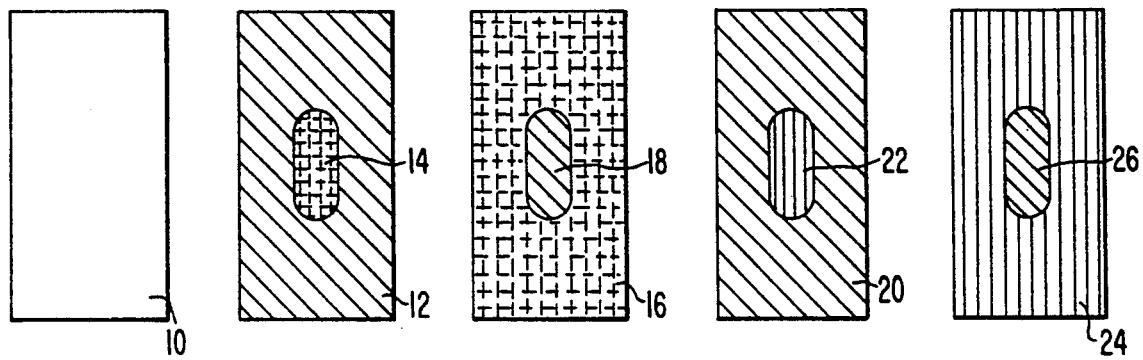
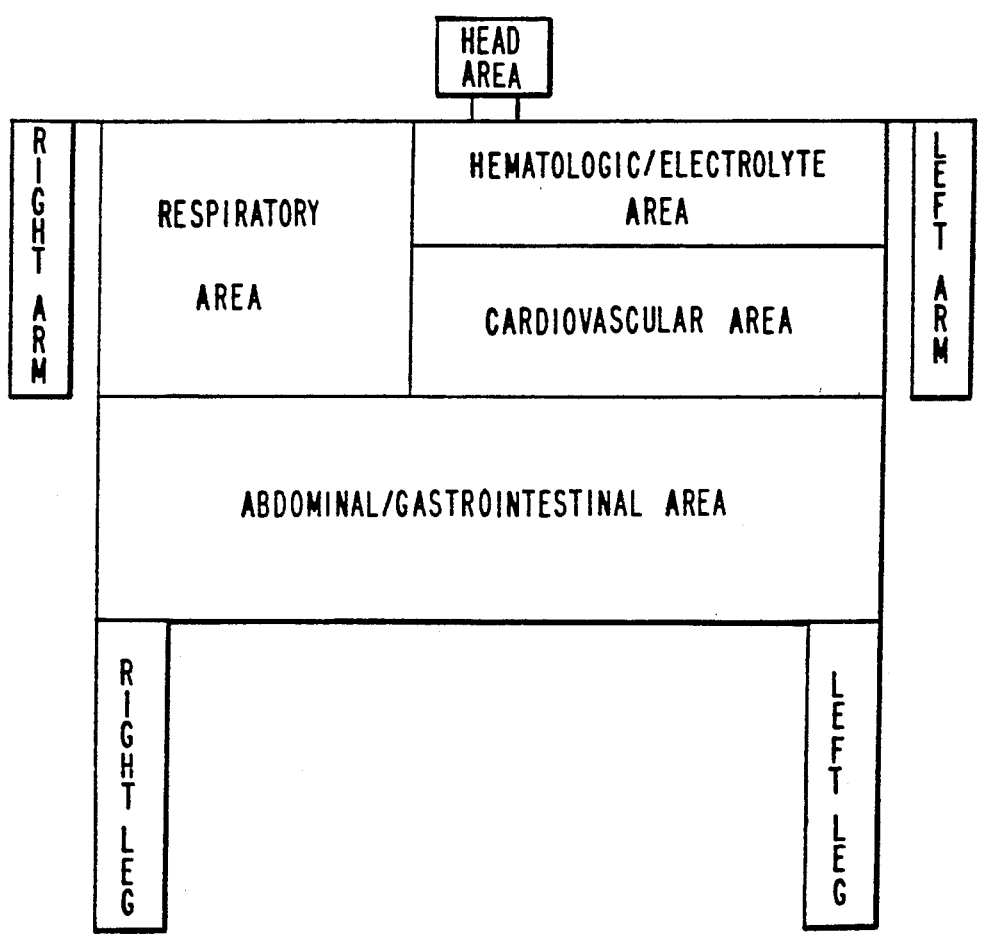

| HEADACHE | | | AVERAGE TEMP | PEAK TEMP |
|---|---|---|---|---|
| RIGHT GAZE | RIGHT PUPIL | MENTAL STATUS | LEFT PUPIL | LEFT GAZE |
| RIGHT UPPER SENSORY | RIGHT UPPER MOTOR | NASOGASTRIC TUBE | LEFT UPPER MOTOR | LEFT UPPER SENSORY |
| RIGHT LOWER SENSORY | RIGHT LOWER MOTOR | ENDOTRACHIAL TUBE | LEFT LOWER MOTOR | LEFT LOWER SENSORY |

FIG. 3

| IMV AREA | | | | RESP |
|---|---|---|---|---|
| PEEP AREA | | | | |
| FIO2 AREA | | | | |
| CURRENT pH | CURRENT % $CO_2$ | CURRENT % $O_2$ | CURRENT % SAT | CURRENT BASE EX |
| HIGH/LOW pH | HIGH/LOW % $CO_2$ | HIGH/LOW % $O_2$ | HIGH/LOW % SAT | HIGH/LOW BASE EX |
| AVERAGE pH | AVERAGE % $CO_2$ | AVERAGE % $O_2$ | AVERAGE % SAT | AVERAGE BASE EX |

FIG. 4

| Na+ | K+ | Mg++ | BUN |
|---|---|---|---|
| Cl- | CO$_2$-- | Glu | Cr |

| PT | aPTT |
|---|---|
| Hgb | Hct |
| WCB | Plts |

BLOOD WORK

FIG. 5

| CURRENT HR | CURRENT BP | CURRENT CI | CURRENT PCWP | CURRENT SVR | NSR OR A FIB | |
|---|---|---|---|---|---|---|
| HI/LOW HR | HI/LOW BP | HI/LOW CI | HI/LOW PCWP | HI/LOW SVR | PAC's | PVC's |
| AVERAGE HR | AVERAGE BP | AVERAGE CI | AVERAGE PCWP | AVERAGE SVR | SVT | AFIB |
| | | CK | CK-MB | | V TACH | V FIB |

FIG. 6

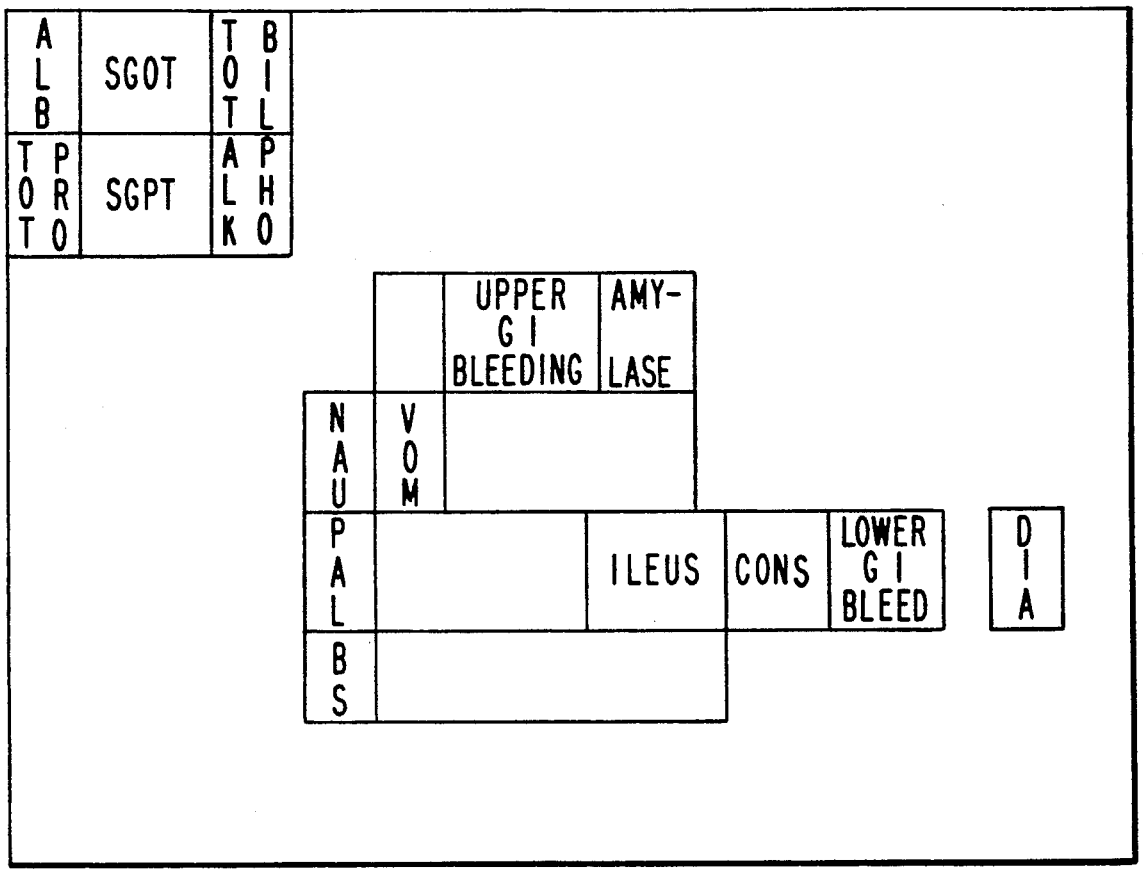
FIG. 7
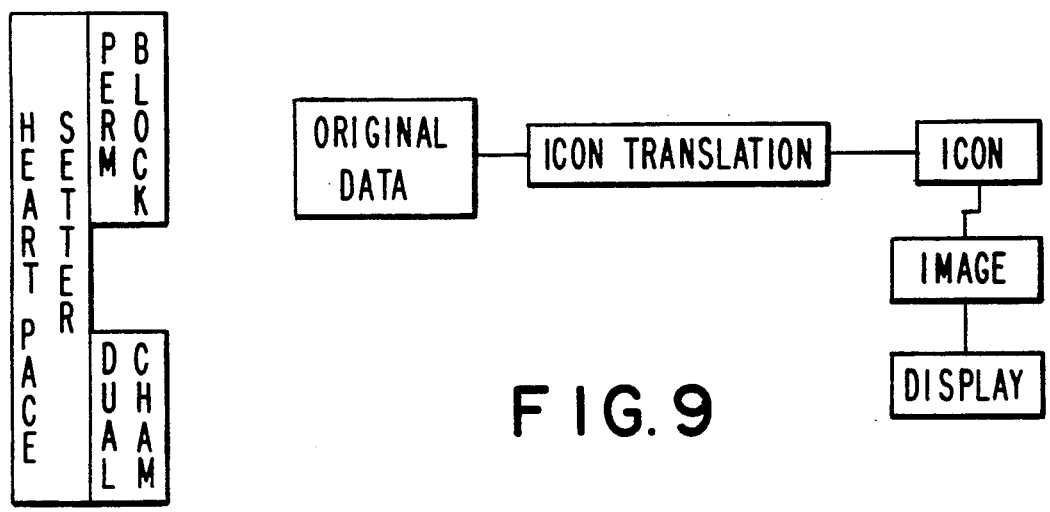
FIG. 8
FIG. 9

GRAPHICAL LANGUAGE METHODOLOGY FOR INFORMATION DISPLAY

This application is a continuation application of Ser. No. 07/440,877, filed Nov. 24, 1989, now abandoned.

BACKGROUND OF THE INVENTION

The advent of computer systems for information acquisition, as well as the increasingly information intensive society in which we live, result in decision makers routinely being required to assimilate larger and larger amounts of information, much of which, in fact, is produced by automated information gathering systems. Unfortunately, this information load continues for the most part to be reported as alphanumeric information, either in printed reports or via other display systems such as computer terminals. The human brain, however, is a better image processor than it is a calculator or character processor. Thus, while the brain is capable of assimilating and using alphanumeric information, it more rapidly assimilates images. It is, therefore, desirable that new methodologies of data display be developed which take advantage of these processing characteristics of the human brain.

Barriers to rapid understanding also result from language differences. For example, although people worldwide recognize the image of a chair, its description in textual form appears different in different languages. Similarly, descriptions of more complex datasets also appear different because of the different characters sets used around the world to describe them.

With regard to the practice of medicine, physicians around the world make decisions based on substantially the same information, for example values of electrolytes, hemoglobin, etc. However, the representations of such information in, for example, Japanese are likely to be totally unintelligible to a physician conversant in only English.

SUMMARY OF THE INVENTION

The present invention seeks to overcome these problems by further processing information, characterized in standard datasets, into displays, or "Lessergrams," comprised of those datasets translated into symbol or icon based images, or "Charlottes," so as to facilitate the user's ability to assimilate large amounts of interrelated information directly into conscious understanding. The present invention sets forth information in a display with details of the information identified by features of the display such as location, color, size, form, and intensity. With this display methodology, barriers to information acquisition are substantially reduced. By creating a standard format for such displays, the advantages of this display methodology are enhanced. If different image representations for the same knowledge base were utilized, then the resulting displays would merely exchange alphanumeric language differences for image based language differences. As a result, much of the inherent advantage of image based display methodologies would be lost. Therefore, the present invention also seeks to create standards of image creation so as to avoid barriers of image translation associated with language differences.

The present invention is, thus, a method of icon based information presentation. An embodiment of the invention as applied to a medical information display system for use, for example, in a medical intensive care unit is described; however, other embodiments and applications are within the scope of the invention. The described embodiment solves problems created by the necessity for the modern physician to assimilate the tremendous amounts of information developed in modern intensive care units during the daily care of a patient and the additional requirement that this information typically must be assimilated by numerous care givers in this environment. In addition, typically information must be acquired from a large number of sources including, for example, the patient, nurses, laboratory sources, support equipment, and various patient monitoring devices. The methodology creates a single display that can almost instantaneously transmit tremendous amounts of information regarding the patient's status and therapies that otherwise would be presented in alphanumeric and/or binary form. If desired, to ease the learning process associated with understanding the patient information presented in image form in accordance with the present invention, the visual images can be accompanied by alphanumeric information.

In accordance with the present invention, a complete display is constructed from icon-based images of standard medical datasets, including for example monitoring device data (blood pressure, pulse rate, etc.), electrolyte levels, arterial blood gas levels, liver function tests, etc. An image is developed for each dataset based on the specific values assigned to individual datapoints in each dataset, or, in the case of binary information (e.g., therapeutic treatment such as the presence or absence of an intravenous line, or other corrective intervention), based on the presence or absence of that particular device. The images are subsequently plotted into standard locations on the display to create a complete display for visualization and analysis by a physician. In the described embodiment, the patient condition information can be keyed into a microcomputer at the patient's bedside, either as alphanumeric information for subsequent processing and image translation or directly as image information using physicians or paramedical personnel to process the information and create the correct image by entering the necessary commands directly from the keyboard.

BRIEF DESCRIPTIONS OF THE DRAWINGS

These and other aspects and advantages of the present invention are more apparent from the following detailed description and claims, particularly when considered in conjunction with the accompanying drawings. In the drawings:

FIGS. 1A-1E depict illustrative icons, including modulated icons, usable in a display system and method in accordance with a preferred embodiment of the present invention;

FIG. 2 illustrates general image locations for a display presenting various anatomical datasets in accordance with a preferred embodiment of the present invention;

FIG. 3 illustrates a dataset of the head region usable in the display of FIG. 2;

FIG. 4 illustrates a respiratory dataset usable in the display of FIG. 2, including details of an arterial blood gas dataset;

FIG. 5 illustrates hematologic and electrolyte datasets usable in the display of FIG. 2;

FIG. 6 illustrates a cardiovascular dataset usable in the display of FIG. 2;

FIG. 7 illustrates an abdominal/gastrointestinal dataset usable in the display of FIG. 2;

FIG. 8 illustrates an image of a heart pace setting device which can be incorporated into the display of FIG. 2; and FIG. 9 illustrates a method of creating of an image from a dataset in accordance with the present invention.

DETAILED DESCRIPTION OF A PREFERRED EMBODIMENT

The teachings of the current invention are applicable to creation of a display from any information source which produces alphanumeric and/or binary information, including alphanumeric representations of information which are associated as "words." The only requirement for the production of a display is to define the specific datapoints to be contained in each image, to assign specific locations for each image on the display, and then to decide on the methodology (color, intensity, size, presence or absence, shape/form modulation, or any combination of these) to be used to describe different valuations for members of a given dataset. In the described preferred embodiment, green icons are used to designate normal conditions, red icons to designate abnormally high values, and yellow icons to designate abnormally low values. Value modulation is indicated by changing a portion of a green icon to red or yellow. In some displays, e.g. those in the supraventricular tachycardia icon, frequency of occurrence of an event is indicated by modulating the amount of color in a given icon. In addition, corrective intervention such as therapeutic devices, for example vascular lines, catheters, other tubes, etc., which can be attached to or in the patient, are detailed with white icons in specifically defined locations. Blue icons are used to describe infections of certain organs or organ systems, again on the basis of location on the display. In other areas of the display, e.g. in the corrective intervention area, various types of intervention are designated by color and/or form of the icon, as well as by location. For example, medical therapeutic intervention such as inotropes, which are a class of medications including dopamine, dobutamine, epinephrine, norepinephrine, etc., can have the same form/color icon representation, but have respective locations on the display that uniquely identify each. In addition, medication route (i.e. oral or intravenous) is detailed by icon location.

In a preferred embodiment, information obtained on a given patient includes such information as the presence or absence of various vascular lines (e.g., peripheral or central IV's), catheters, and tubes (e.g., endotracheal, nasogastric, chest, and intra-aortic balloons), etc., as well as various blood parameters (e.g., electrolytes, hemograms, clotting factors, liver function tests, cardiac enzymes, etc.), physical exam findings (e.g., neurological findings, findings about the chest, the cardiac system, the extremities, etc.), vital signs, input and output systems, (e.g., urine, gastrointestinal, etc.), daily weights, etc., all of which are entered into the display system either in alphanumerical form for subsequent analysis by the system which then assigns and plots the appropriate icons, or directly as icons from the keyboard via specifically programmed keys actuated by physicians or other paramedical personnel. As new information is obtained, or previously recorded information changes, new values are assigned to the various icons comprising each display. For various binary icons (e.g., presence or absence of a foley catheter), the representative image is simply removed from the display when the device is removed from the patient. Thus, all caregivers viewing the display obtain immediate knowledge of the patient's overall condition, including the level of instrumentation. In addition to having value from a caregiver's standpoint, this has additional value for those doing acuity assessments.

FIG. 1A depicts the basic icon 10, which is displayed in the color green to indicate a normal condition, red to indicate a dangerously high condition, or yellow to indicate a dangerously low condition. Modulations are accomplished with the use of color, with each basic icon form being identical. Thus, FIG. 1B depicts a green icon 12 having a yellow center 14 to indicate a slightly low abnormality, while FIG. 1C depicts a yellow icon 16 with a green center 18, indicating a moderately low abnormality. A solid yellow icon, thus, indicates a very low abnormality. Similarly, FIG. 1D depicts a green icon 20 with a red center 22 to indicate a slightly high abnormality, FIG. 1E depicts a red icon 24 with a green center 26 to indicate a moderately high abnormality, and a solid red icon indicates a very high abnormality. Dangerously low or high levels are indicated by causing the yellow or red icon to blink or flash. Further refinement of the slightly and moderately abnormal level indications can be provided by appropriately modulating the size of the center 14, 18, 22, or 26 within the abnormal icon 12, 16, 20, or 24.

FIG. 2 depicts the basic display consisting of a "stick figure" representing the head, body areas, arms and legs of a patient. The head image is detailed in FIG. 3 and consists of icons representing parameters including average and peak temperatures, gaze, and pupil activity, as well as upper and lower extremity motor and sensory functions. Additionally included in this image are illustrative device icons representing a naso-gastric tube and an endotracheal tube. A "mental status" icon indicates the consciousness level of the patient, including whether the patient is alert and awake, somnolent, comatose, or agitated. Head pain or "headache," which is a symptom or compliant, is also depicted by an icon.

FIG. 2 also depicts general areas within the body display where images indicating datasets from the various systems are plotted. These correspond roughly to the general anatomical locations of the particular systems, thereby assisting in visualization and assimilation of the information in the display. The general respiratory images, depicted in FIG. 4, include datasets indicating details such as ventilator settings, respiratory rate, arterial blood gases, and lung exam icons. Details of the blood gas display are also shown.

FIG. 5 depicts images regarding datasets indicating blood work, specifically hemogram and electrolytes, which could be considered "central" as compared to specific system blood work, such as liver function tests (vide infra), cardiac isozymes, etc. Additionally, previously acquired information is "dated" by presenting it in an icon adjacent the current icon, providing within the image comparative information and so allowing the caregiver to assimilate progress of the patient.

FIG. 5 includes details of hemogram and electrolyte images. Of particular note is the magnesium "Mg++" icon in the electrolyte dataset. This is displayed even though it is not considered a standard part of a "SMA6" (a standard electrolyte profile) or a "SMA7" (another standard profile which adds creatinine to the SMA6). The display shows the tremendous advantage of creating standard datasets and images. In the typical alphanumeric or chart based information systems, a caregiver evaluating the patient must closely examine the patient chart, or in a computer based system must "pull up" the value of magnesium, to determine whether required tests have been performed. In the system of the present invention, the presence or absence of the "Mg++" icon immediately gives the caregiver this information. Thus, not only the presence of icons, but also their absence in a given image, transmits information.

The cardiovascular dataset image, detailed in FIG. 6 includes, for example, heart rate, blood pressure, cardiac index, pulmonary capillary wedge pressure, vascular resistance, and the associated rhythm image consisting of occurrence icons or images for premature atrial and ventricular contractions, supraventricular tachycardia and atrial fibrillation, ventricular tachycardia, and ventricular fibrillation. Additionally contained within the cardiovascular section of the display are the cardiac isoenzyme, and physical exam images. As can be seen, current, high/low, and average indications can be presented for varying parameters.

FIG. 7 depicts the image of the abdominal/gastrointestinal area dataset. The liver dataset is displayed in the displayed stick figure's right upper quadrant, which is the general anatomical location of the liver. In this image, datapoint icons are located so as to readily show the various "sub-conditions" that can occur with respect to the liver, e.g., acute hepatocellular disease would appear much differently than a biliary obstructive type process. The gastrointestinal system image is also designed to have an appearance generally similar to the actual gastrointestinal system. FIG. 7 additionally shows how images can be created that transmit related but variable source multiparametric datapoints from, e.g., laboratory sources, (amylase), physical examination ("Pal"—palpation, "BS"—bowel sounds), patient complaints ("Nau"—nausea), observed phenomena ("Vom"—vomiting, "Dia"—diarrhea), etc. This reveals the true power behind this information display methodology. Physicians can recognize complex patient conditions as simple images. Several blank or unused icon locations are included in FIG. 7 to accommodate additional phenomena.

FIG. 8 depicts an image representing a heart pacesetting device or "Pacemaker." Device icons are preferably displayed in white. For the most part they are binary, i.e., present or absent. However, they can also be modulated, as are other datapoint icons, to describe a specific datapoint, e.g., present but with an abnormal function. Specifically, an abnormally functioning device, such as an abnormally functioning heart pace setting device, may be modulated with black. Further refinements of the preferred embodiment might include methodologies for further modulation. In the current example, modulation might be required to describe an abnormal "sense", or abnormal "pace" function of a pace setting device.

FIG. 9 illustrates the method of creating images. Simply stated, a given datapoint falls in a certain range which is translated into the datapoint icon. This icon is then combined in a standard fashion with other icons in the dataset to produce an image.

Obviously, in light of the above noted teachings, numerous variations of the present invention with respect to the content of particular datasets or images, their forms, indicator colors, intensities or sizes could be created by those skilled in the art. In addition, the preferred embodiment is only one of many knowledge domains from which standardized datasets can be developed. It is therefore to be recognized and understood that the invention may be practiced or applied otherwise than as specifically described herein. For example, it might be applied to display data concerning business financial information, engineering data and/or measurements, data from construction or assembly process monitoring or weather systems monitoring, flight information, or air traffic control data. The display of FIG. 2 can be modified as desired, for example by adding images indicating the condition of the neck, shoulder, knee or other body part. Further, an image on a small scale display such as in FIG. 2 can represent a single bodily part, for example a foot which has been fractured, and a separate, enlarged display can be called up with images that present indications of the conditions of the several bones, the cartilage, etc. within the foot. Thus, although the present invention has been described with reference to preferred embodiments, rearrangements and substitutions can be made, and still the result will be within the scope of the invention.

What is claimed is:

1. A method of generating a display for a database of information on a physical system, the display including a plurality of display segments of fixed size, shape and display location, the physical system having a plurality of datapoints, said method comprising the steps of:
   (a) assigning each datapoint to a display segment to cause the display segments to present an image having a morphological arrangement approximating the physical system;
   (b) monitoring the value of each datapoint;
   (c) determining the variation in the value of each datapoint from a normal value for the datapoint;
   (d) assigning preselected display figure icons to indicate various degrees of variation in the value of a datapoint from a normal value for the datapoint;
   (e) providing display figure icons to the display segments in accordance with the determined variations in the values of the associated datapoints from normal values for the respective datapoints so that the color configurations of the respective display segments indicate the variations of the values of the associated datapoints from the normal values for such datapoints, and the datapoints are identifiable from their respective display locations; and
   (f) displaying the resulting image.

2. A method as claimed in claim 1 wherein step (d) comprises assigning the display figure icons in a first color configuration to indicate a normal status for the associated datapoint and in a second color configuration to indicate a dangerously abnormal status for the associated datapoint.

3. A method as claimed in claim 1 wherein step (d) comprises assigning the display figure icons in a first color configuration to indicate a normal status for the associated datapoint, in a second color configuration to indicate a moderately abnormally high status for the associated datapoint, in a third color configuration to indicate a very high status for the associated datapoint, in a fourth color configuration to indicate a moderately abnormally low status for the associated datapoint, and in a fifth color configuration to indicate a very low status for the associated datapoint.

4. A method as claimed in claim 3 further comprising causing the display figure icon of a display segment associated with a datapoint having a dangerously abnormal status to blink.

5. A method as claimed in claim 1 wherein step (b) includes acquiring data indicative of corrective intervention performed on the physical system, and step (d) includes assigning a predefined display figure icon to indicate the corrective intervention.

6. A method as claimed in claim 1 wherein step (b) comprises acquiring data indicative of the physical condition of a human patient.

7. A method as claimed in claim 6 wherein step (b) includes acquiring data indicative of therapy which the patient is receiving, and step (d) includes assigning a predefined display figure icon to indicate the therapy.

8. A method as claimed in claim 1, wherein step (d) comprises assigning different display figure icons to indicate datapoint conditions of normal, slightly low, moderately low, very low, dangerously low, slightly high, moderately high, very high, and dangerously high for numeric bounded data; and step (e) comprises providing to each display segment associated with a datapoint having numeric bounded data a display figure icon indicating the condition of the associated datapoint as determined from the monitored value of that datapoint.

9. A method as claimed in claim 1, wherein step (d) comprises assigning different display figure icons to indicate datapoint conditions of normal, slightly abnormal, moderately abnormal, and very abnormal for non-numeric-bounded data; and step (e) comprises providing to each display segment associated with a datapoint having non-numeric-bounded data a display figure icon indicating the condition of the associated datapoint as determined from the monitored value of that datapoint.

10. A method as claimed in claim 1, wherein step (d) comprises assigning different display figure icons to indicate presence and absence of binary datapoint conditions; and step (e) comprises providing to each display segment associated with a datapoint having a binary condition a display figure icon indicating the condition of the associated datapoint as determined from the monitored value of that datapoint.

11. A method as claimed in claim 1, wherein step (d) comprises assigning different display figure icons to indicate the frequency of occurrence of ongoing event data; and step (e) comprises providing to each display segment associated with a datapoint having ongoing event data a display figure icon indicating the condition of the associated datapoint as determined from the monitored value of that datapoint.

12. A method as claimed in claim 1, wherein step (d) comprises assigning different display figure icons to indicate datapoint conditions of presence of infection and absence of infection; and step (e) comprises providing to each display segment associated with a datapoint for infection data a display figure icon indicating the condition of the associated datapoint as determined from the monitored value of that datapoint.

13. A method as claimed in claim 1, wherein step (d) comprises assigning different display figure icons to indicate datapoint conditions of presence and absence of corrective intervention; and step (e) comprises providing to each display segment associated with a datapoint having corrective intervention data a display figure icon indicating the condition of the associated datapoint as determined from the monitored value of that datapoint.

* * * * *